US00PP16389P3

(12) United States Plant Patent
Larsen

(10) Patent No.: US PP16,389 P3
(45) Date of Patent: Mar. 28, 2006

(54) ***OSTEOSPERMUM* PLANT NAMED 'SUNNY MARY'**

(50) Latin Name: *Osteospermum ecklonis*
Varietal Denomination: Sunny Mary

(75) Inventor: Bjarne Nyholm Larsen, Odense N (DK)

(73) Assignee: Sunny Osteospermum Aps, Odense N (DK)

( * ) Notice: Subject to any disclaimer, the term of this patent is extended or adjusted under 35 U.S.C. 154(b) by 8 days.

(21) Appl. No.: 10/873,228

(22) Filed: Jun. 23, 2004

(65) Prior Publication Data

US 2005/0022279 P1 Jan. 27, 2005

(30) Foreign Application Priority Data

Jul. 7, 2003 (EM) ..... 2003/1239

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Foley & Lardner, LLP

(57) ABSTRACT

A new distinct cultivar of *Osteospermum* plant named 'Sunny Mary', characterized by its large upright purple inflorescences, ray floret colors: Ray florets from RHS 71A, red-purple with stripes of RHS 59A, purple to RHS 67A red-purple with stripes of RHS 72A, red-purple; dense and bushy plant form, mainly due to more upright stems; and compact plant habit; moderately vigorous growth habit, but less need for chemical growth retardation; and fewer and smaller inflorescences per plant.

3 Drawing Sheets

Genus and species of the plant claimed: *Osteospermum ecklonis* (DC) T. Norl.
Variety denomination: 'Sunny Mary'.

BACKGROUND OF THE INVENTION

The present Invention relates to a new and distinct cultivar of *Osteospermum* plant, botanically known as *Osteospermum ecklonis* (DC) T. Norl., commonly known as Cape Daisy and hereinafter referred to by the variety denomination 'Sunny Mary'.

The new *Osteospermum* is a product of a planned breeding program conducted by the Inventor, Bjarne Larsen, in Stige, Denmark. The new *Osteospermum* originated from a cross made in 2000 by the Inventor between *Osteospermum ecklonis* (DC) T. Norl. designated '9913' (unpatented) and *Osteospermum ecklonis* (DC) T. Norl. designated '90.018.00' (unpatented). The Inventor selected the new *Osteospermum* cultivar from the progeny of the above crossing in 2001 on the basis of its inflorescence color and compact, freely branching habit. Plants of the new *Osteospermum* are upright, compact and have a unique color.

Asexual reproduction of the new cultivar by terminal cuttings taken and propagated in trial production batches in Stige, Denmark, has shown that the unique features of this new *Osteospermum* are stable and reproduced true to type in many successive generations.

SUMMARY OF THE INVENTION

The following traits have been repeatedly observed and are determined to be the unique characteristics of 'Sunny Mary'. These characteristics in combination distinguish 'Sunny Mary' as a new and distinct cultivar:

1. large upright purple inflorescences, ray floret colors: ray florets from RHS 71A, red-purple with stripes of RHS 59A, purple to RHS 67A, red-purple with stripes of RHS 72A, red-purple;
2. dense and bushy plant form, mainly due to more upright stems; and compact plant habit;
3. moderately vigorous growth habit, but less need for chemical growth retardation; and
4. fewer and smaller inflorescences per plant.

Plants of the cultivar 'Sunny Mary' can be compared to plants of the *Osteospermum ecklonis* (DC) T. Norl. Cultivar 'Sunny Nathalie' (unpatented). However, in side-by-side comparisons conducted by the Inventor in Stige, Denmark, plants of the cultivar 'Sunny Mary' and the cultivar 'Sunny Nathalie' differ in the following characteristics:

1. Plants of the new *Osteospermum* have striking color combinations of deep purple to red ray florets and violet-blue disk with orange pollen.
2. Plants of the new *Osteospermum* have fewer leaves and longer internodes than plants of the cultivar 'Sunny Nathalie'.
3. Plants of the new *Osteospermum* have shorter and thinner peduncles than plants of the cultivar 'Sunny Nathalie'.
4. Plants of the new *Osteospermum* are shorter and more compact than plants of the cultivar 'Sunny Nathalie'.
5. Plants of the new *Osteospermum* have less, but smaller inflorescences per plant than the plants of the cultivar 'Sunny Nathalie'.

Plants of the cultivar 'Sunny Mary' can be compared to plants of the parental cultivars '9913' and '90.018.00'. Plants of the cultivar 'Sunny Mary' differ from plants of the parental cultivars, '9913' and '90.018.00', primarily in inflorescence color.

Plants of the cultivar 'Sunny Mary' have not been observed under all possible environmental conditions. The phenotype may vary somewhat with variations in environment such as temperature, light intensity, day length, and fertility level without, however, any variance in genotype.

BRIEF DESCRIPTION OF THE PHOTOGRAPHS

The accompanying colored photographs illustrate the overall appearance of the new *Osteospermum* cultivar 'Sunny Mary' showing the colors as true as is reasonably possible with colored reproductions of this type. Colors in the photographs may differ slightly from the color values cited in the detailed botanical description which accurately describe the color of the new *Osteospermum* cultivar 'Sunny Mary'.

The first photograph shows a side perspective view of a typical flowering plant of 'Sunny Mary' as grown in an 11 cm pot.

The second photograph is a close-up, top view of the young and older inflorescences.

The third photograph shows the detail of front and back of a 'Sunny Mary' inflorescence as well as the front and back of the leaf.

DETAILED BOTANICAL DESCRIPTION

In the following description, color references are made to The Royal Horticultural Society Colour Chart (R.H.S.), 4$^{th}$ edition. Plants were grown under greenhouse conditions. Plants used for this description were grown for about 20 weeks after cutting.

Botanical classification: *Osteospermum ecklonis* (DC) T. Norl.

Parentage:

*Female parent.*—*Osteospermum ecklonis* (DC) T. Norl. designated '9913' (unpatented).

*Male parent.*—*Osteospermum ecklonis* (DC) T. Norl. designated '90.018.00' (unpatented).

*Propagation.*—Type cutting: terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial plant with upright plant habit. *Osteospermum* flowers in composite heads. Freely branching with lateral flowering branches forming at every node; dense and bushy.

*Crop time.*—After rooting, about 18 weeks are required to produce finished flowering plants in 11 cm pots.

*Plant height* (*soil level to top of plant plane*).—About 18 cm.

*Plant diameter.*—18 cm.

*Vigor.*—Moderately vigorous growth rate.

Foliage description: Leaves alternate, single, pinnate venation. Length: 4–8 cm. Width: About 30 mm. Shape: Obovate. Apex: obtuse; Apex (young leaf): acute. Base: attenuate to decurrent. Margin: broadly lobed. Texture: smooth, glabrous, shiny. Scattered short, stiff hairs. Color: Young foliage, upper and lower surfaces: RHS 147B, yellow-green. Mature foliage, upper surface RHS N147A, mature foliage lower surface RHS 148A. Venation, RHS 148B.

Inflorescence description:

*Inflorescence arrangement and shape.*—Tubular disk and (ligulate) ray florets in composite daisy capitulae; with 15 parted small involucre. Thin (2 mm) peduncles.

*Natural flowering season.*—Continuous throughout the spring and summer in temperate regions. Season can be extended by vernalization and long day treatments.

*Inflorescence longevity on the plant.*—5 to 9 days (longevity of individual inflorescences is highly dependent on temperature and light conditions). Inflorescences persistent, ray florets folding and withering slowly to RHS 79A, dark purple.

*Inflorescence diameter.*—About 5 cm.

*Inflorescence depth.*—Typical: 6 mm. Observed: 4–8 mm.

*Inflorescences.*—Ray Florets: Typical number of ray florets per inflorescence: 18. Observed number of ray florets per inflorescence: 18. Length: Ray florets: About 20 mm. Width (diameter): Maximum about 7–8 mm. Ray floret apex: elliptic, acute. Ray floret base: fused. Ray floret margin: entire. Ray floret color: Upper surfaces (when opening): RHS 71A, red-purple with stripes of RHS 59A, purple; underside (when opening): RHS N81A, purple-violet with stripes of RHS 83A, violet. Upper surface (fully opened): RHS 67A, red-purple with stripes of RHS 72A, red-purple; under surfaces (fully opened): RHS N79A, purple, with stripes of RHS N79C, purple.

*Disk florets.*—Typical number of disks florets per inflorescence: 60. Observed number of disks florets per inflorescence: 45–70. Length: Disk florets: About 6 —mm. Width (diameter): About 3 mm. Disk floret overall shape: tubular. Disk floret free tips apex: Attenuate. Disk floret base: Fused. Disk floret tip margin: entire. Disk floret color: Upper surfaces: tips RHS N89B, violet-blue; basal tube RHS 75D, light purple; to RHS 155A, white. Underside: RHS 155A, white.

*Phyllary.*—Observed number of phyllaries: 13–17 Typical number of phyllaries: 15. Length: 4–6 mm. Width: 1–3 mm. Overall shape: lanceolate. Apex shape: acuminate. Base shape: fused. Margin: entire. Color: Upper surface: RHS 145B to 145A, yellow-green, edges translucent; lower surface: RHS 145A yellow-green, edges translucent.

Reproductive organs:

Androecium:

*Location.*—Disc florets only.

*Anthers.*—Linear fused, stamen color RHS 202A, black.

*Pollen.*—RHS 26A, orange.

Gynoecium:

*Location of gynoecium.*—Ray and disc florets.

*Pistil and stigma.*—Typical pistil number: 1. Observed pistil number: 1. Stigma color: RHS 16C, yellow-orange.

*Peduncle.*—Strength: Moderately strong. Length: About 5 cm. Diameter: About 2 mm. Color: RHS 144C, yellow-green.

*Seed.*—Length: About 1 mm. Diameter: About 0.3 mm.

Disease/pest resistance: Good.

Disease/pest susceptibility: Low.

Weather tolerance: Plants of the new *Osteospermum* have exhibited good tolerance to draught, rain and wind, however flowering may cease during hot periods (temperatures above 30° C. (85° F.)). Low temperature tolerance to −1° C. (30° F.).

I claim:

1. A new and distinct cultivar of *Osteospermum* plant named 'Sunny Mary', as illustrated and described herein.

* * * * *

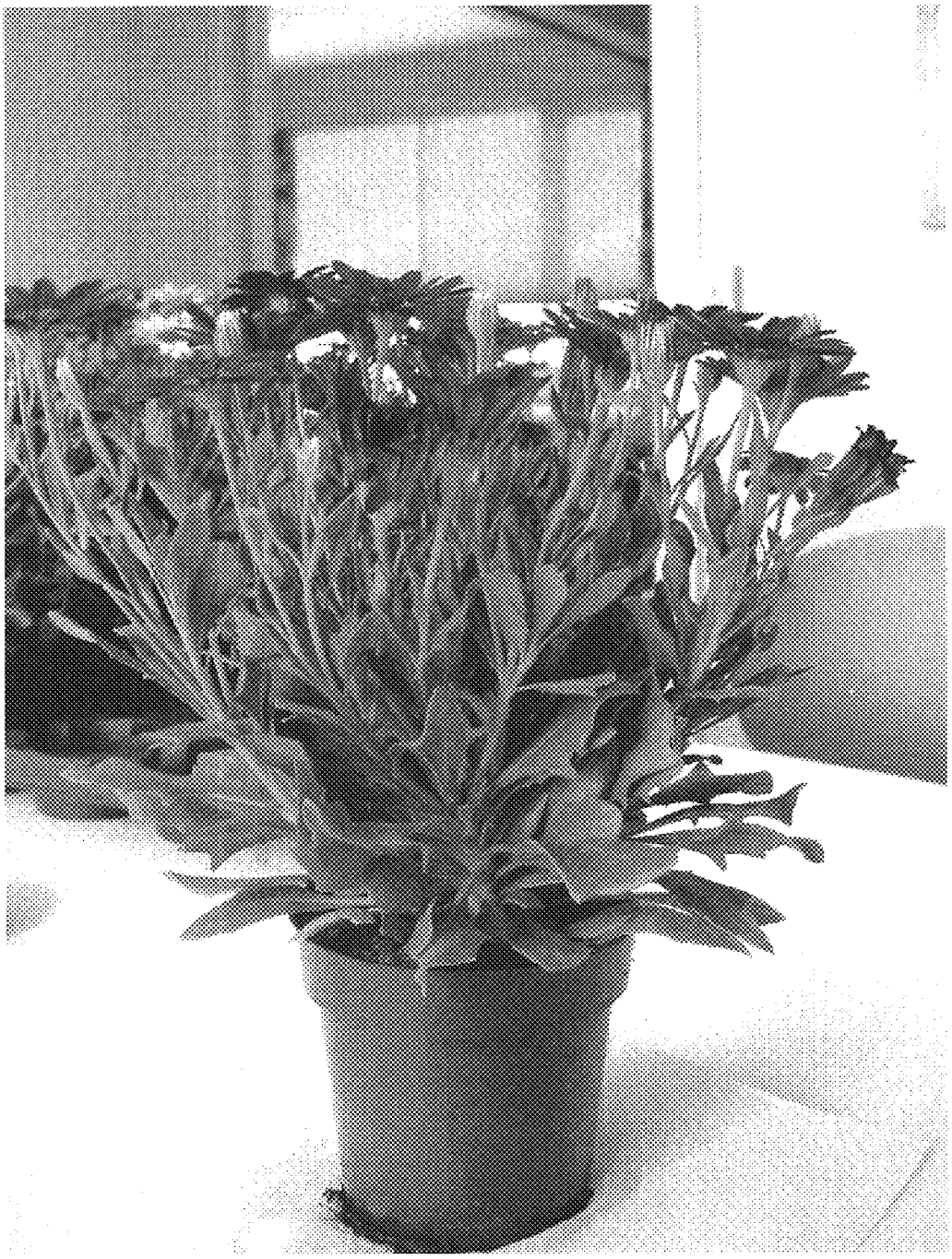

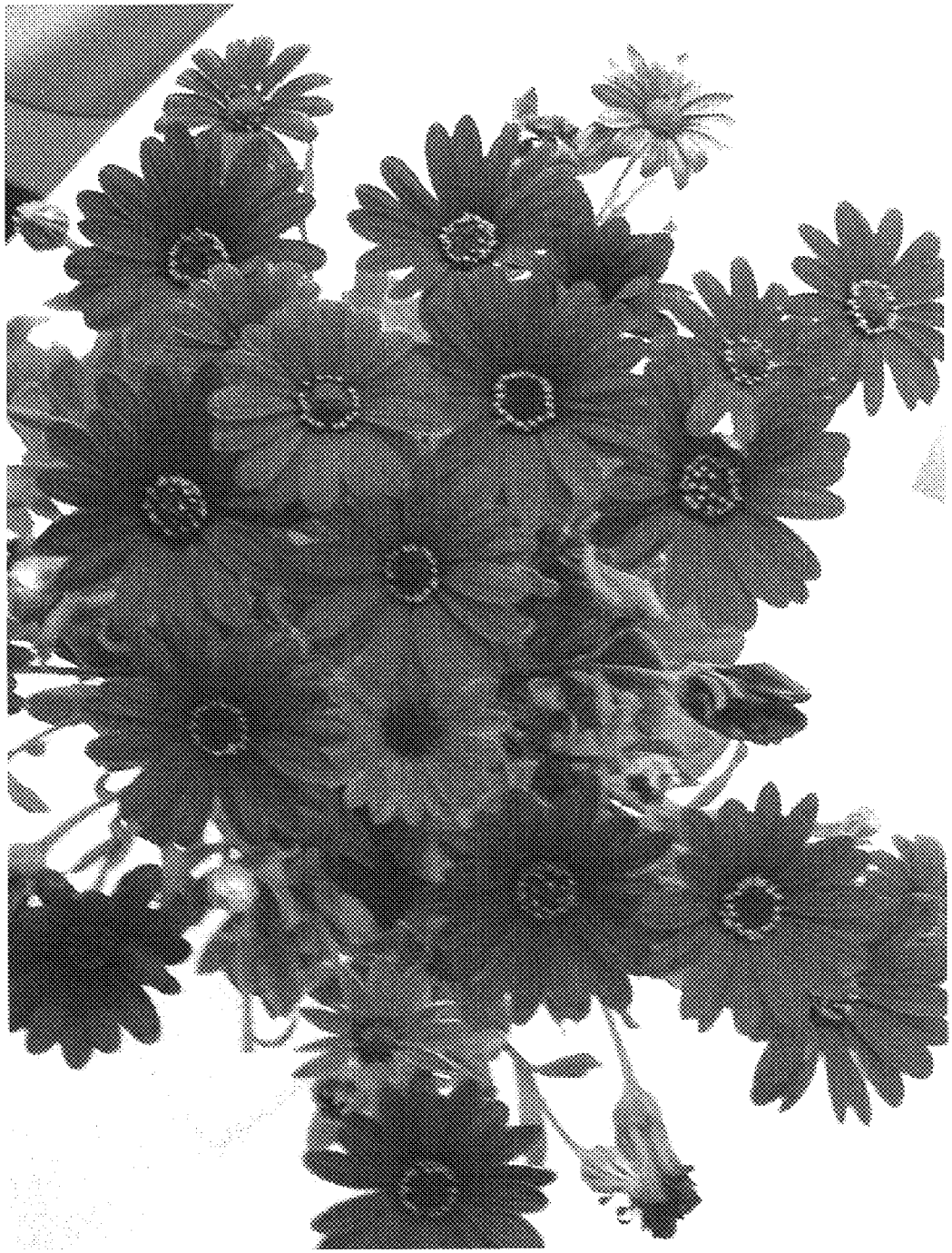

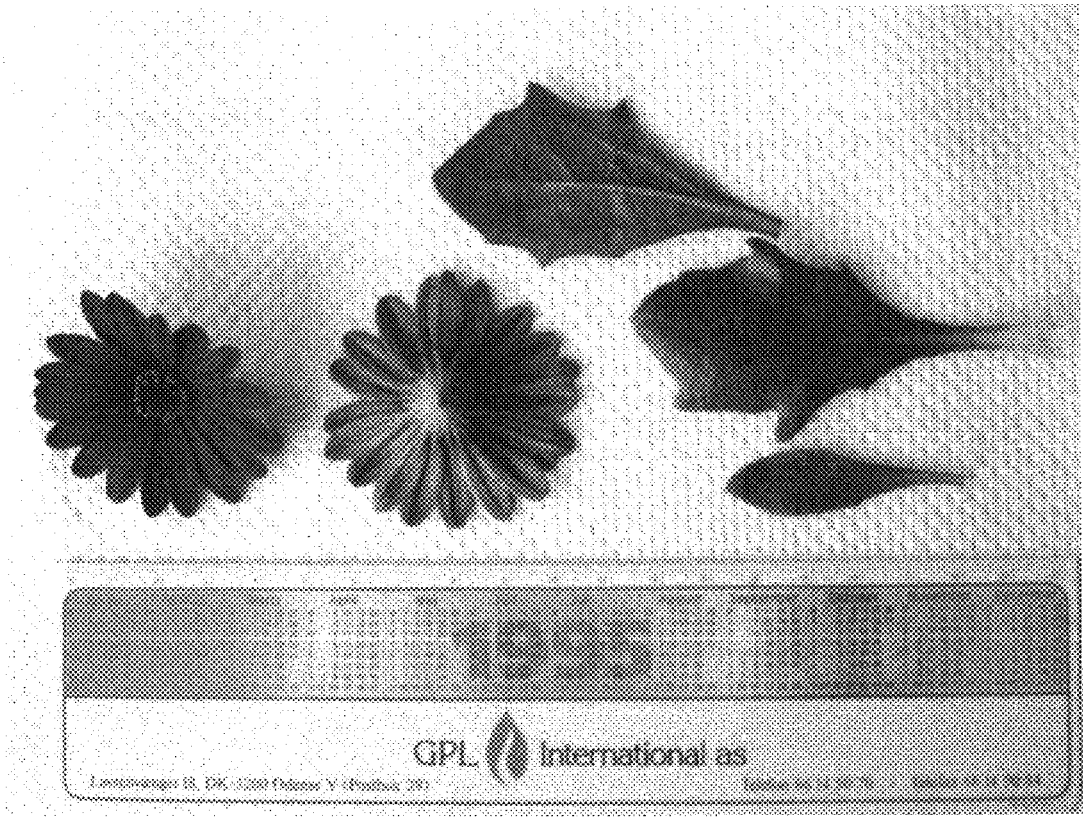
GPL International as